United States Patent
Christensen

(10) Patent No.: US 9,408,965 B2
(45) Date of Patent: Aug. 9, 2016

(54) METHOD AND SYSTEM FOR HANDLING AND TRANSPORTING SYRINGES

(71) Applicant: Tolmar, Inc., Fort Collins, CO (US)

(72) Inventor: Joseph Anders Christensen, Scottsdale, AZ (US)

(73) Assignee: Tolmar, Inc., Fort Collins, CO (US)

( * ) Notice: Subject to any disclaimer, the term of this patent is extended or adjusted under 35 U.S.C. 154(b) by 0 days.

(21) Appl. No.: 14/927,892

(22) Filed: Oct. 30, 2015

(65) Prior Publication Data

US 2016/0121042 A1    May 5, 2016

Related U.S. Application Data

(60) Provisional application No. 62/073,701, filed on Oct. 31, 2014.

(51) Int. Cl.
```
B65D 83/10    (2006.01)
A61M 5/00     (2006.01)
B65D 25/10    (2006.01)
A61B 19/02    (2006.01)
```

(52) U.S. Cl.
CPC ............. A61M 5/008 (2013.01); B65D 25/108 (2013.01); *A61B 19/0271* (2013.01)

(58) Field of Classification Search
USPC ................... 206/365, 366, 370, 562; 422/300
See application file for complete search history.

(56) References Cited

U.S. PATENT DOCUMENTS

| | | | |
|---|---|---|---|
| 4,978,510 A | 12/1990 | Smith | |
| 5,133,939 A | 7/1992 | Mahe | |
| D387,874 S | 12/1997 | Vila | |
| D479,329 S | 9/2003 | Sanguinetti | |
| 8,100,263 B2 * | 1/2012 | Vanderbush | A61M 5/002 206/366 |
| 8,485,357 B2 * | 7/2013 | Song | A61M 5/008 206/366 |
| 8,939,288 B2 * | 1/2015 | Gagnieux | A61M 5/002 206/366 |
| 2007/0151882 A1 * | 7/2007 | Cocheteux | A61M 5/008 206/366 |
| 2010/0139215 A1 | 6/2010 | Van Roy | |
| 2012/0118777 A1 * | 5/2012 | Kakiuchi | A61M 5/002 206/366 |
| 2012/0193256 A1 * | 8/2012 | Gagnieux | A61M 5/008 206/366 |
| 2013/0001117 A1 | 1/2013 | Liversidge | |
| 2013/0177381 A1 * | 7/2013 | Josef | A61M 5/008 414/802 |
| 2013/0186793 A1 | 7/2013 | Gagnieux et al. | |
| 2014/0027326 A1 | 1/2014 | Peruzzo | |
| 2014/0078854 A1 | 3/2014 | Head et al. | |
| 2014/0102927 A1 | 4/2014 | Liversidge | |

OTHER PUBLICATIONS

U.S. Appl. No. 29/507933, Oct. 31, 2014, Christensen.
"Nested Syringe Filling—FXS 2020," VertMarkets, Inc. 2006, 2 pages [retrived from: http://www.pharmaceuticalonline.com/doc/nested-syringe-filling-mdash-fxs-2020-0001].
"Schott Prefillable Glass Syringes," Adelphi Healthcare Packaging, 2011, 1 page [retrieved from: http://www.adelphi-hp.com/en/products/syringes-pipettes/prefillable-syringes/glass.html].

* cited by examiner

*Primary Examiner* — Jacob K Ackun

(74) *Attorney, Agent, or Firm* — Sheridan Ross P.C.

(57) ABSTRACT

A method and system for use in the transportation, sterilization and handling of syringe barrels includes a tray having an array of apertures. The tray comprises features for interfacing with other features such as bins whereby the tray is supported generally horizontally and one or more syringes may be lowered into the tray.

20 Claims, 4 Drawing Sheets

METHOD AND SYSTEM FOR HANDLING AND TRANSPORTING SYRINGES

This U.S. Non-Provisional patent application claims the benefit of priority from U.S. Provisional Patent Application Ser. No. 62/073,701, filed Oct. 31, 2014, the entire disclosure of which is hereby incorporated by reference.

FIELD OF THE INVENTION

Embodiments of the present invention relate to handling syringes. More specifically, embodiments of the present invention provide methods and systems for handling, transporting, filling, and sterilizing prefillable syringes.

BACKGROUND OF THE INVENTION

Prefilled syringes are increasingly being used as an alternative to vial-based systems. Prefilled syringes have the potential to both minimize the potential of microbial contamination and reduce medication dosing errors, while also providing enhanced convenience and ease of use. Further, the use of prefilled syringes is likely to reduce the amount of overfill when compared to single-dose vials, leading to the optimization of the number of doses that may be obtained from a given volume of the substance to be administered. These advantages of prefilled syringes are especially valuable when the substances to be administered are of a high cost and/or prepared in small quantities.

A safe and effective system for handling and delivery of the prefilled syringes to the patient is required. In particular, a system that is capable of safely handling syringes so as minimize contamination, breakage, mislabeling, etc. is required while still providing an efficient means for handling the syringes.

SUMMARY OF THE INVENTION

Accordingly, there has been a long-felt and unmet need to provide a syringe handling system with enhanced user-friendliness, that is easy to manufacture, and reduces the risks of human error. Accordingly, embodiments of the present invention contemplate providing syringe handling devices and systems with preferred and predetermined dimensions such that syringes are received and handled in a predetermined manner.

Embodiments of the present invention relate to the combination of a plurality of syringe barrels and a handling system. Embodiments of the present invention are suitable for use in the course of the manufacture and preparation of syringes to be pre-filled with a drug for subsequent injection.

Preparation and manufacture of pre-filled syringes of the present invention comprises loading of a plurality of syringe barrels into a tub or bin useful for storage and transport purposes. Syringes may be moved in the tub to a location where the syringe barrels will be filled with a predetermined drug or substance and fitted with a stopper and a plunger, the stopper and plunge being known devices useful for dispensing and/or injecting the drug. Embodiments of the present invention contemplate the provision of a tray adapted for use with the tubs. Trays of the present invention comprise a plurality of apertures arranged in an array. Embodiments of the present invention contemplate a tray with a specific and fixed spacing of apertures such that the exact center of each syringe barrel is known, relative to the tub. Additionally, various embodiments of the present invention contemplate that one of a width and a length of the tray is greater than the other, and that tubs for use with the trays comprise similar or corresponding dimensions such that the tray(s) can be fit within the tub(s) in only limited and predetermined orientations, thereby reducing risks of human errors and ensuring the tray(s) are aligned properly with the tub(s). Such alignment is preferable for various filling and sterilization procedures.

Embodiments of the present invention provide for a system for preparing syringes and syringe barrels under sterile conditions, and loading the syringes into a tray supported in a tub. When the tray is fully loaded, the tub may be sealed with a cover and, if desired, packed with a plurality of tubs for storage, shipment, etc. When the syringe barrels are to be loaded with a drug, the syringe barrels are removed from an open tub by a mechanical handling system. The system must be able to ascertain the precise position of the tub and of the center of each aperture in the tray supported within the tub.

In various embodiments of the present invention, needle devices are supported in a tray or tray device by a support or shelf portion extending laterally away from apertures provided in the tray. In certain embodiments, first and second support portions are provided on opposing sides of an aperture and spaced apart 180 degrees. The support portions generally correspond in size, shape, and/or positioning such that the finger flange or grip portions of the syringe that extend away from the barrel may be received and supported by the support portions. In such embodiments, apertures of the tray are of sufficient size to allow the barrel portion and a needle shield (i.e. a needle shield fitted to the syringe, a shield of a safe needle device fitted to the syringe or a needle hub) to pass therethrough in a case where the device, hub or shield has a greater diameter than that of the syringe body or barrel. Additionally, the specific arrangement of the support portions and limited options for providing syringes within apertures dictates that syringes are provided within the tray in a specific orientation, thereby reducing packing errors and associated problems.

An enlargement of a syringe barrel may be integrally formed with the syringe barrel and may thus comprise an outwardly projecting flange formed at the user-proximal end of the syringe barrel to facilitate the performance of an injection with the syringe. Alternatively, the enlargement may be separately formed and then fitted to the syringe barrel, typically adjacent a flange provided at the rear end of the syringe barrel. In certain embodiments of the present invention, the support surfaces are sized to securely receive and secure the enlargement or finger flange portions of the syringe with a tight tolerance, thereby reducing the possible movement and/or rotation of the syringe when it is provided in an aperture.

In certain embodiments, apertures comprise a downwardly extending sidewall which may extend below the flange portion of the tray. The downwardly extending sidewall is adapted to receive at least a portion of a syringe barrel and prevent lateral movement and/or rotation about a horizontal axis of the syringe.

The provision of support members comprising a fixed position relative to a remainder of the tray provides for various quality assurances and process control features, particularly during filling operations wherein centers of the syringe barrels must be known and fixed.

Embodiments of the present invention extend to a combination as described above in conjunction with a cover member for a container carrying a tray and syringe barrels, the cover member being sealingly secured to the free edge of the side wall of the container, remote from the face thereof. The invention further extends to a syringe barrel for use in a combination of this invention as described above and also to a tray for use in such a combination, as described above.

Various embodiments of the present invention relate to systems, methods and devices for packing syringes in trays or "trays". In various embodiments, trays or trays comprise features and means for securing or holding syringes in a desired orientation, wherein a plurality or syringes are spaced apart and provided a position that is suitable for at least one of filling, transporting and sterilizing of the syringe(s). Preferably, when multiple syringes are provided on a single tray, the syringes are provided in an ordered, spaced apart manner wherein each of said syringes are provided at substantially the same orientation. Various embodiments of the present invention contemplate providing syringes in such relative positions and orientations so as to avoid contact between syringes, particularly during transport, and to allow or adequate space between adjacent syringes to facilitate filling and sterilization of adjacent syringes.

In various embodiments, trays comprise syringe transport and containment devices generally made from polypropylene. The trays comprise a base plate provided with a plurality of apertures. In certain embodiments, the apertures comprise sidewalls or tubes extending therefrom in the same direction through which the syringes are fitted, and the sidewalls comprising a height. Known syringes are generally provided with a collar with a diameter greater than that of the syringe. In various embodiments, apertures provided in the trays comprise diameters that are greater than a diameter of a barrel of the syringe(s) to be contained, but smaller than a maximum dimension of the collar of the syringe(s) to be contained. Syringes are typically provided in this arrangement in the tray without a stopper or plunger provided therein, to allow for sterilization and filling of the syringe barrel.

Various known syringes comprise barrel members that comprise a glass material, such as a borosilicate glass for example. Such glass materials are suitable for storing materials within a prefilled or prefillable syringe, as syringe contents are known to be less reactive with glass materials than other known materials such as plastics and metals. Glass, however, is also known to suffer from the drawbacks of being a generally brittle material subject to fracture and breakage. Accordingly, trays of the present invention contemplate devices that are capable of securing syringes in a safe manner wherein the syringes are at least somewhat protected from various impacts and the risks of breakage are substantially reduced.

Various embodiments of the present invention provide for trays or trays with wells provided as receiving features for syringes. In certain embodiments, wells are designed and sized so as to receive only a particular type of syringe, and thereby reduce the risks of mishandling, mislabeling, mistakes in filling, etc.

In one embodiment, a handling system for a plurality of syringes is provided, the system comprising a tray having an array of apertures provided therethrough, each of the apertures adapted for receiving a syringe barrel and an associated needle shield. The tray comprises a support surface extending around each of the apertures and configured to support the weight of a syringe in at least one position. The tray comprises a length and a width, the length and the width being substantially perpendicular, and the width being greater than the length. Each of the apertures are spaced apart along the length and the width, wherein adjacent apertures in a width direction are spaced farther apart than adjacent apertures in a length direction. A first plurality of ribs extends along the width direction, and a second plurality of ribs extends along the length direction, wherein the first plurality of ribs comprise a greater thickness than the second plurality of ribs, and the support surface extends in only one of the width direction and the length direction such that a syringe may only be provided in an aperture in a first orientation or a second orientation and wherein the second orientation is characterized by a 180 degree rotation of said syringe from said first orientation.

In yet another embodiment, a tray for handling a plurality of syringes is provided, the tray comprising an array of wells adapted for receiving a plurality of syringes, wherein each of the wells comprises an aperture and a support surface configured to support a weight of a syringe in at least one position. The tray further comprises a rectangular shape having a length and a width, the length and the width being substantially perpendicular. A flange extends around a perimeter of the tray, the flange comprising an upper surface and a lower surface and wherein the lower surface is adapted to contact a tub. Each of the apertures is spaced apart along the length and the width. A first plurality of ribs extends along the width direction, and a second plurality of ribs extending along the length direction, wherein the first plurality of ribs comprise a greater thickness than the second plurality of ribs. The support surface extends in only one of the width direction and the length direction such that a syringe may only be provided in an aperture in a predetermined orientation.

In yet another embodiment, a tray for handling a plurality of syringes is provided, the tray comprising an array of wells adapted for receiving a plurality of syringes. The array of wells is at least partially defined by a first plurality of ribs and a second plurality of ribs. The tray comprises a rectangular shape having a length and a width, the length and the width being substantially perpendicular. The first plurality of ribs comprises a plurality of ribs extending in a length direction and wherein the ribs are parallel to one another. The second plurality of ribs extends in a width direction and being parallel to one another and perpendicular to the first plurality of ribs. The first plurality of ribs comprise a greater thickness than the second plurality of ribs. Wells are provided between intersecting ribs, each of the wells comprising a recessed rectangular shape with an aperture provided therein and a support surface configured to support a weight of a syringe in at least one position. A flange extends around a perimeter of the tray, the flange comprising an upper surface and a lower surface and wherein the lower surface is adapted to contact a tub. Each of said apertures are spaced apart along said length and said width. The support surface extends in only one of said width direction and said length direction such that a syringe may only be provided in an aperture in a predetermined orientation, and wherein rotation of a syringe is substantially prevented when provided within an aperture in the tray.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

BRIEF DESCRIPTION OF THE DRAWINGS

The drawings constitute a part of this specification and include exemplary embodiments of the present invention and illustrate various objects and features thereof.

DETAILED DESCRIPTION OF THE INVENTION

It is to be understood that while certain forms of the present invention have been illustrated and described herein, it is not to be limited to the specific forms or arrangement of parts described and shown.

Figure 1:
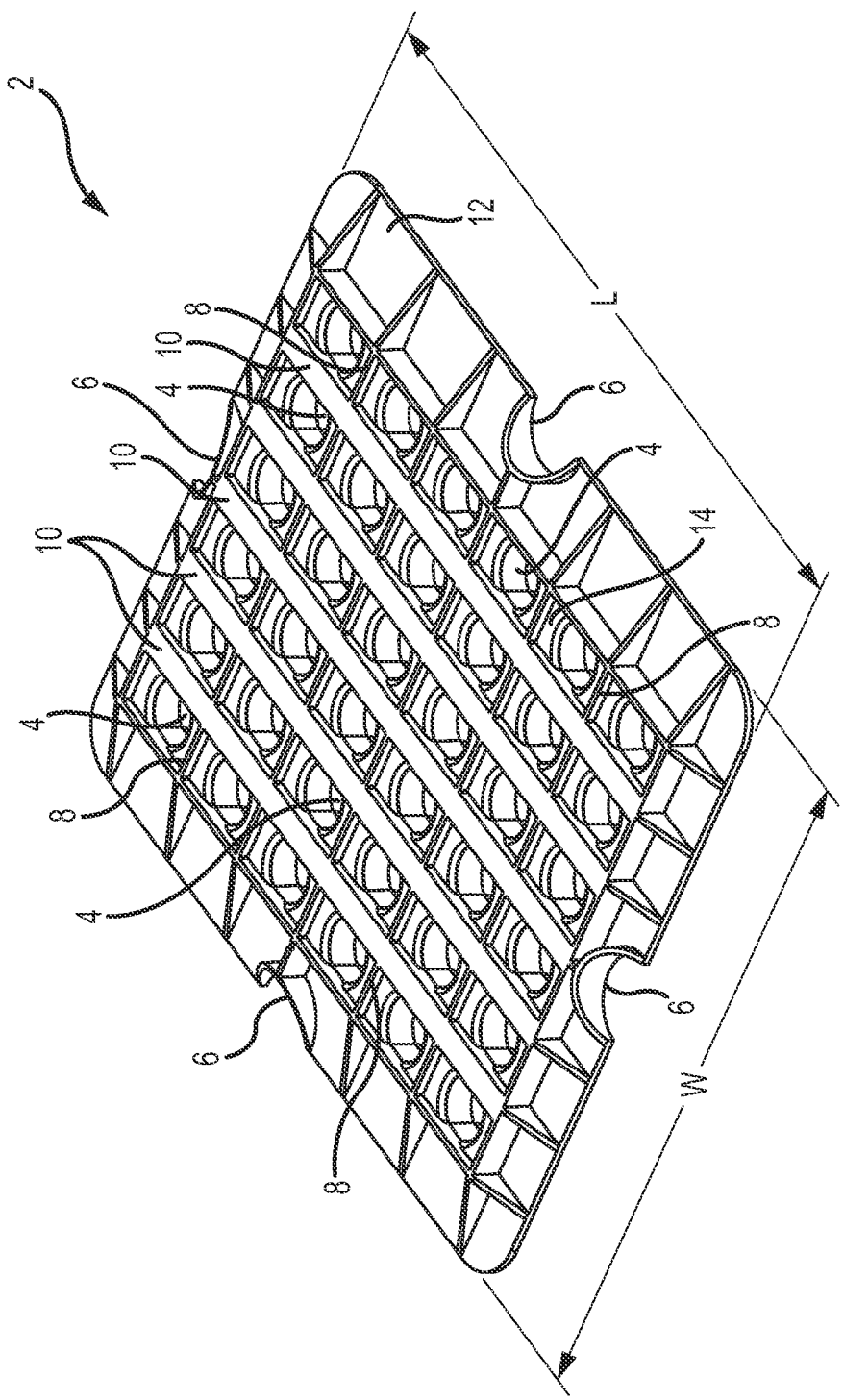
FIG. 1 is a front perspective view of a syringe tray according to one embodiment of the present invention.

As shown in FIG. 1, a nest or tray 2 is provided comprising a plurality of wells 4 for receiving syringes. As shown, the plurality of wells 4 is provided in an array. In the depicted embodiment, a 6×6 array of thirty six wells 4 are provided for receiving up to thirty six syringes. The tray 2 comprises a length L and a width W. The length L and the width W of the embodiment of FIG. 1 may be substantially equivalent, thus forming a substantially square tray 2. It will be recognized, however, that the present invention is not limited to any particular dimensions or proportions. In preferred embodiments of the present invention, various dimensions of the tray are dictated by various considerations, including standard sizing of additional components and features with which the tray 2 is designed to interface. For example, in certain embodiments of the present invention, trays 2 are provided that are designed to interface and/or interconnect with a tub suitable for sterilizing syringes provided in the tray 2. Accordingly, trays 2 of the present invention are provided comprising a width W between approximately 150 millimeters and 250 millimeters and a length L between approximately 150 millimeters and 250 millimeters. In preferred embodiments, trays 2 of the present invention are provided comprising a width W between approximately 190 millimeters and 200 millimeters (and preferably about 195.93 mm) and a length L between approximately 220 and 230 millimeters (and preferably about 228.93 mm).

In various embodiments, trays 2 of the present invention comprise recesses 6 to allow a user to grasp and manipulate the tray 2. In the depicted embodiments, the tray 2 comprises a recess on each of the four sides, in preferred embodiments, trays 2 comprise at least two recesses 6, each of said recesses provided on opposing sides of the tray 2.

As shown, the tray 2 preferably comprises a plurality of upstanding rib members 8, 10 to provide structural support for the tray 2 and/or provide spacing between adjacent wells 4. As shown, a plurality of rib members 10 are provided as extending in a longitudinal or length L direction. A second plurality of rib members 8 are provided as extending in the transverse or width W direction. In the depicted embodiment, the first plurality of rib members 10 comprise a thickness that is greater than the thickness of the second plurality of rib members. In various embodiments, the first plurality of rib members comprises a thickness of between approximately 7.0 and 10.0 millimeters. In preferred embodiments, the rib members 10 comprise a thickness of between approximately 8.0 and 9.0 millimeters, and more preferably of 8.59 millimeters. It will be recognized, however, that the present invention is not limited to trays having rib members of any particular thickness or other dimension.

A flange member 12 extends around a perimeter of the tray 2, the flange member 12 comprising a substantially planar lip or boundary of the tray 2. The flange member 12 provides a user interface as well as a contact point for providing the tray 2 in contact with a tub, for example.

The wells 4 comprise apertures extending through the tray 2 and are adapted to receive a syringe, at least a portion of the syringe comprising a circular cross-section. Known syringes typically comprise a finger grip portion provided on an end of the syringe proximal to a user. Trays 2 of various embodiments of the present invention comprise wells 4 wherein each well 4 is adapted for receiving a syringe. The wells 4 comprise a substantially circular-shaped sidewall 5 surrounding a void area or aperture. A syringe support surface or shelf portion 14 is provided external to the aperture, the shelf portion(s) 14 comprising an area for receiving a portion of a syringe, such as a finger grip portion extending laterally from the syringe. In preferred embodiments, the shelf portions 14 extend outwardly from the aperture of the well 4 in only one axis, while a second perpendicular axis of the well 4 is bounded by rib members 10. Such an arrangement provides for securing of syringes wherein the rib members 10 substantially prevent rotation of the syringe by contacting the finger grip or tab portion(s) of the syringe. The shelf portions 14, which generally comprise a recessed rectangular shape defined by surrounding rib members 8, 10 in the embodiment depicted in FIG. 1, also provide a support for a portion of a syringe to be received such that the syringe is prevent from passing completely through the well 4. The wells 4 and shelf portions 14 are preferably recessed from surrounding rib members 8, 10.

Figure 2:
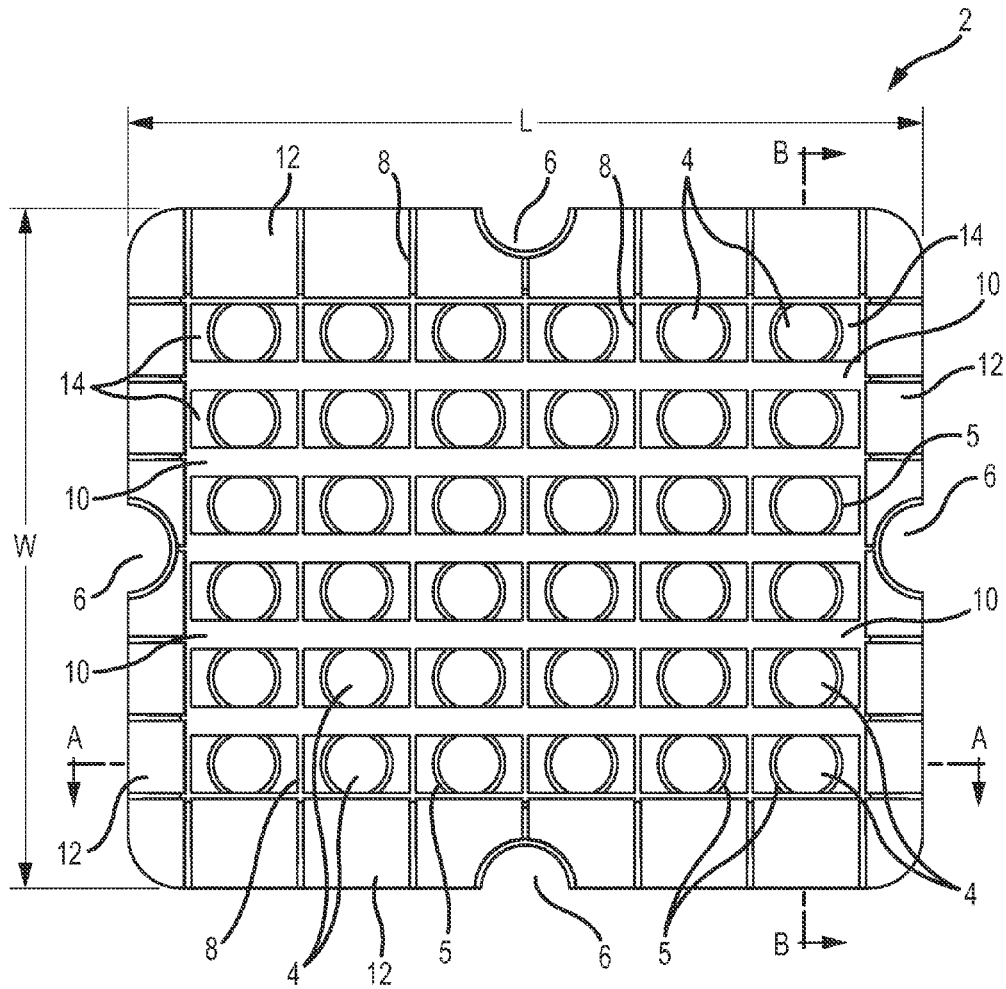
FIG. 2 is a top plan view of the syringe tray according to the embodiment of FIG. 1.

FIG. 2 is a top plan view of a tray 2 according to the embodiment of FIG. 1. As shown, a plurality of wells 4 are provided in an array within the tray 2. The wells 4 are separated from adjacent wells 4 in the width direction by at least the thickness of the first rib members 10. The wells are separated or spaced apart from adjacent wells 4 in the length direction by second rib members 8 and shelf portion 14 which extend outwardly from a diameter of the wells 4 in at least the length direction L. The wells 4 are thus provided in a spaced apart array or grid. In certain embodiments, the center of each well 4 is spaced from the center of an adjacent well 4 by between approximately 20.0 and 30.0 millimeters in the width direction W. In preferred embodiments, the center of each well 4 is spaced from the center of an adjacent well 4 by between approximately 22.5 and 25.0 millimeters in the width direction W, and most preferably by approximately 24.89 millimeters. In certain embodiments, the center of each well 4 is spaced from the center of an adjacent well 4 by between approximately 25.0 and 40.0 millimeters in the length direction L. In preferred embodiments, the center of each well 4 is spaced from the center of an adjacent well 4 by between approximately 30.0 and 35.0 millimeters in the length direction L, and most preferably by approximately 32.39 millimeters.

Figure 3:
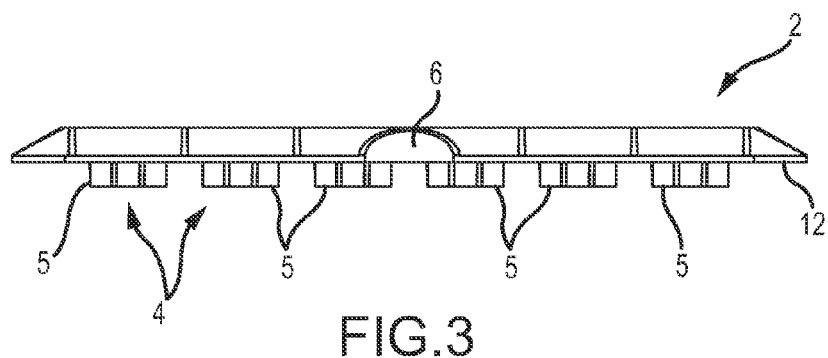
FIG. 3 is a side elevation view of the syringe tray according to the embodiment of FIG. 1.

FIG. 3 is a side elevation view of a tray 2 according to the embodiments of FIGS. 1 and 2. As shown, sidewalls 5 of the wells 4 extend downwardly from the flange member 12 of the tray 2. The wells 4 comprise hollow cylinders having a length for receiving tubular barrels of syringes (not shown in FIG. 3), the length suitable for securing syringes and to substantially prevent movement of the syringes when placed in the wells 4.

In various embodiments, the sidewalls 5 of the wells 4 extend below a lowermost portion of the flange member 12 by at least approximately 5.0 millimeters, and preferably by approximately at least 7.0 millimeters. In various embodiments, the sidewalls 5 of the wells 4 extend below an uppermost portion of the tray 2 by at least approximately 15.0 millimeters, and preferably by approximately at least 17.0 millimeters.

Figure 4:
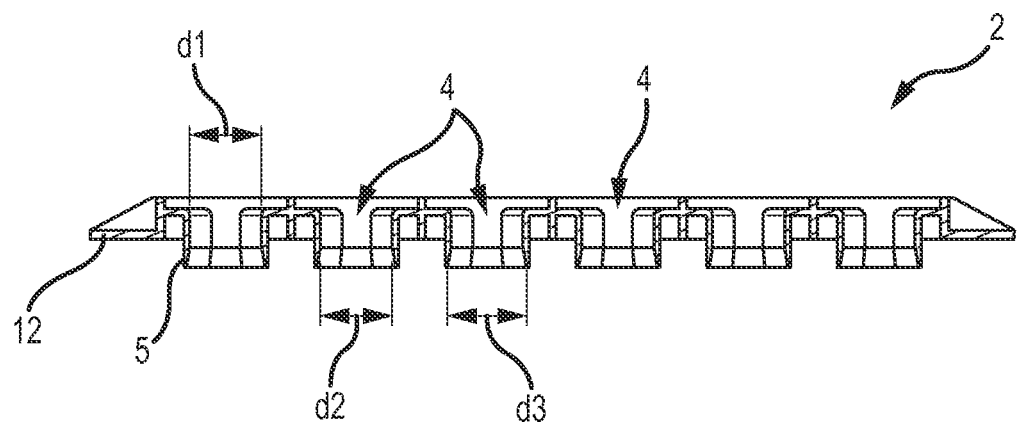
FIG. 4 is a cross-sectional elevation view of the syringe tray according to the embodiment of FIG. 1 and taken at line A-A of FIG. 2.

FIG. 4 is a cross-sectional elevation view of the syringe tray according to the embodiment of FIG. 1 and taken at line A-A of FIG. 2. As shown, a plurality of wells 4 comprising apertures and downwardly extending sidewalls 5 are provided and spaced apart in a length direction. In various embodiments, wells 4 of the present invention comprise a first internal diameter d1 of between approximately 15 millimeters and 20 millimeters. In preferred embodiments, wells 4 of the present invention comprise a first internal diameter of between approximately 17.50 millimeters and 18 millimeters, and more preferably 17.78 millimeters. In various embodiments, wells 4 of the present invention comprise an outer diameter d3, which is separated from the internal diameter by the sidewall 5, of between approximately 18 millimeters and 22 millimeters. In preferred embodiments, wells 5 of the present invention comprise an external diameter d3 of between approximately 20 millimeters and 21 millimeters, and preferably about 20.34 millimeters. In the depicted embodiment, lower portions of the sidewalk 5 comprise an outward taper. This outward taper results in a larger internal diameter at the lower portion of the sidewall 5. This larger internal diameter is shown as a second internal diameter d2. The second internal diameter in various embodiments is provided as being between approximately 17 millimeters and 19 millimeters. In preferred embodiments, the second internal diameter d2 is provided as between approximately 17.75 millimeters and 18.50 millimeters, and more preferably about 18.06 millimeters. Lowermost portions of the wells are provided in various embodiments to facilitate insertion and removal of syringes from the tray.

Figure 5:
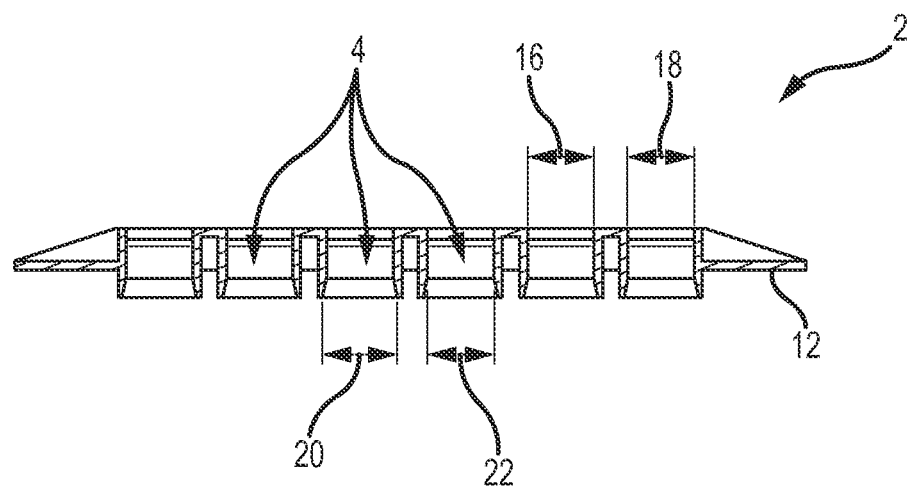
FIG. 5 is a cross-sectional elevation view of the syringe tray according to the embodiment of FIG. 1 and taken at line B-B of FIG. 2.

FIG. 5 is a cross-sectional elevation view of the syringe tray according to the embodiment of FIG. 1 and taken at line B-B of FIG. 2. As shown, a plurality of wells 4 comprising apertures and downwardly extending sidewalk 5 are provided and spaced apart in a width direction. The spacing of the wells 4 in the width direction is smaller than the spacing of the wells 4 in the length direction (as shown in FIG. 4). As shown in FIG. 3, the wells 4 are bounded by the first plurality of rib members 10. In the depicted embodiment, the wells 4 do not form complete circles, but rather comprise substantially cylindrical features wherein linear portions provided by the rib members 10 truncate the circumference of the circle. In various embodiments, wells 4 of the present invention comprise a taper on the upper and lower portion of the well 4.

In the embodiment depicted in FIG. 5, a tray 2 is provided with wells 4, wherein each well 4 comprises a first upper internal diameter 16 that is between approximately 15.0 and 20.0 millimeters. In preferred embodiments, a first upper internal diameter 16 comprises a dimension between approximately 16.0 and 17.0 millimeters, and preferably about 16.30 millimeters. The wells 4 further comprise a second upper internal diameter 18 that is between approximately 15.0 and 20.0 millimeters. In preferred embodiments, a second upper internal diameter 18 comprises a dimension between approximately 16.0 and 17.0 millimeters, and preferably about 16.59 millimeters. Accordingly, the wells 4 of the depicted embodiment comprises a tapered portion proximal an upper end of the well to facilitate insertion and removal of syringes, for example.

In various embodiments, a first lower diameter 20 of the wells 4 comprises a diameter between approximately 15.0 and 20.0 millimeters. In preferred embodiments, a first lower diameter 20 comprises a diameter between approximately 18.0 and 19.0 millimeters, and preferably about 18.86 millimeters. A second lower diameter 22 of the wells 4 comprises a diameter between approximately 15.0 and 20.0 millimeters. In preferred embodiments, a second lower diameter 22 comprises a diameter between approximately 16.0 and 17.0 millimeters, and preferably about 16.58 millimeters. Accordingly, a lower end of the wells 4 also comprises a tapered or funneled portion to facilitate insertion and removal of syringes.

Figure 6:
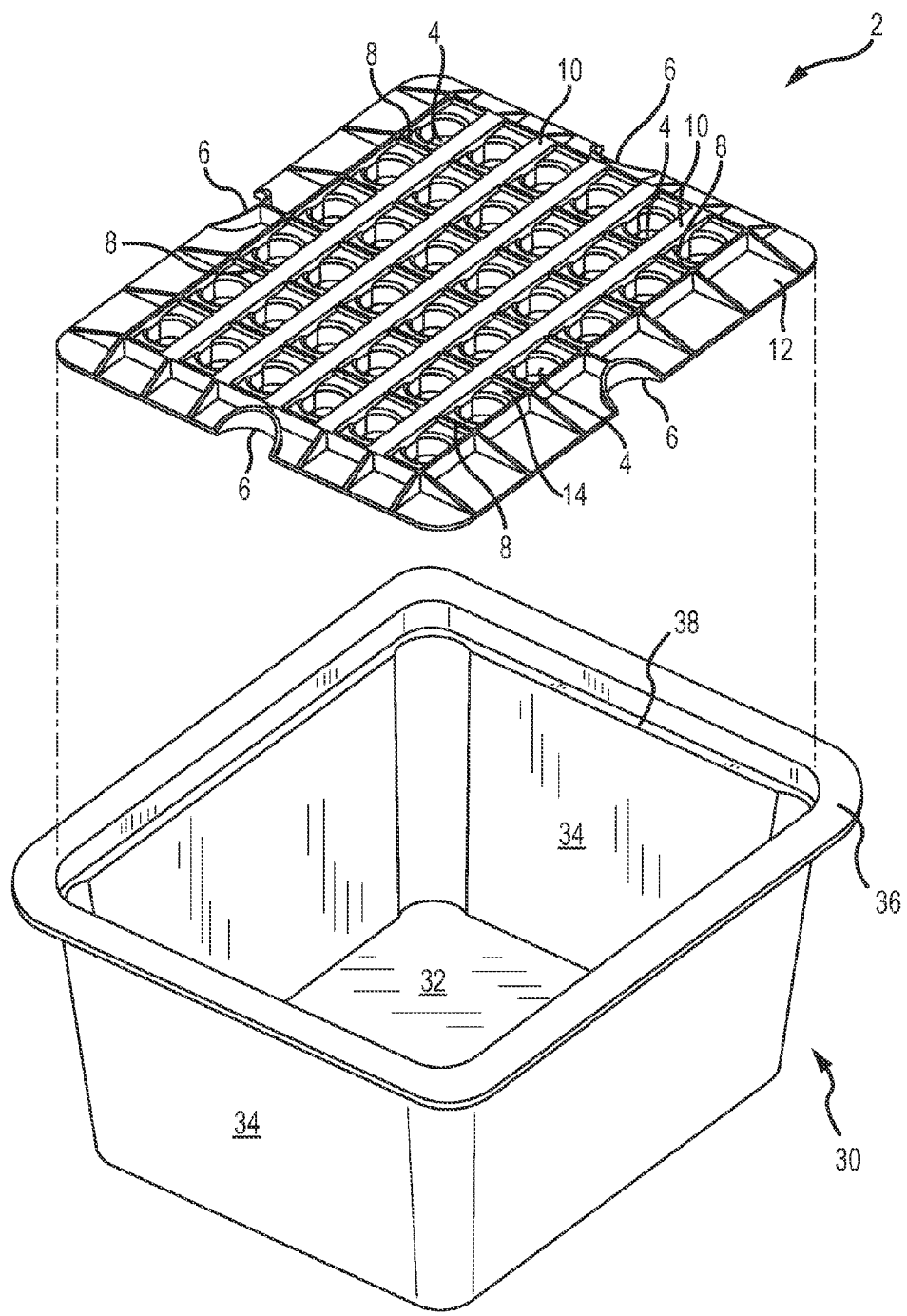
FIG. 6 is a perspective view of a syringe handling system according to one embodiment of the present disclosure.

As shown in FIG. 6, trays in accordance with the present disclosure are adapted to communicate with a tub 30 comprising a base 32 with an upstanding side wall 34 and a lip 36 around an upper periphery of the side wall. A shelf portion 38 is provided internal to the lip 36, the shelf portion 38 adapted to receive and support a tray 2. A cover member may be provided to hermetically seal the tub from an outside environment, at least until access to the tub or tray is desired. The tub 30 comprises a depth that is sufficient to accommodate a plurality of syringes disposed in the tray 2. The tub preferably comprises a depth of between approximately four inches and approximately twelve inches as measured from the shelf portion 38 to a bottom of the tub 30.

While various embodiments of the present invention have been described in detail, it is apparent that modifications and alterations of those embodiments will occur to those skilled in the art. However, it is to be expressly understood that such modifications and alterations are within the scope and spirit of the present invention. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A handling system for a plurality of syringes, the system comprising:
    a tray having an array of apertures provided therethrough, each of said apertures adapted for receiving a syringe barrel and an associated needle shield;
    said tray comprising a support surface extending around each of said apertures and configured to support the weight of a syringe in at least one position;
    said tray comprising a length and a width, said length and said width being substantially perpendicular, said width being greater than said length;
    each of said apertures being spaced apart along said length and said width, wherein adjacent apertures in a width direction are spaced farther apart than adjacent apertures in a length direction;
    a first plurality of ribs extending along said length direction, and a second plurality of ribs extending along said width direction, wherein said first plurality of ribs comprise a greater thickness than the second plurality of ribs; and
    wherein said support surface extends in only one of said width direction and said length direction such that a syringe may only be provided in an aperture in a first orientation or a second orientation and wherein said second orientation is characterized by a 180 degree rotation of said syringe from said first orientation.

2. The handling system of claim 1, wherein said tray further comprises a flange member extending around substantially the entire perimeter of said tray.

3. The handling system of claim 2, further comprising a tub, the flange member comprising a contact surface for contact with said tub and wherein said tub comprises a depth greater than a length of said syringe.

4. The handling system of claim 1, wherein the tray comprises a molded plastic material.

5. The handling system of claim 2, wherein the flange member comprises a plurality of recesses adapted to allow a user to grasp the tray.

6. The handling system of claim 1, wherein the apertures are non-circular.

7. A tray for handling a plurality of syringes, the tray comprising:
   an array of wells adapted for receiving a plurality of syringes;
   wherein each of the wells comprises an aperture and a support surface configured to support a weight of a syringe in at least one position;
   the tray comprising a rectangular shape having a length and a width, the length and the width being substantially perpendicular;
   a flange extending around a perimeter of the tray, the flange comprising an upper surface and a lower surface and wherein the lower surface is adapted to contact a tub;
   each of said apertures being spaced apart along said length and said width;
   a first plurality of ribs extending along said length direction, and a second plurality of ribs extending along the width direction, wherein the first plurality of ribs comprise a greater thickness than the second plurality of ribs; and
   wherein the support surface extends in only one of said width direction and said length direction such that a syringe may only be provided in an aperture in a predetermined orientation.

8. The tray of claim 7, wherein the wells comprise a sidewall, and wherein the sidewall extends downwardly beyond the lower surface of the flange.

9. The tray of claim 8, wherein the sidewalk comprise a first diameter and a second diameter, and wherein the second diameter is greater than the first diameter.

10. The tray of claim 7, wherein the tray comprises a molded plastic material.

11. The tray of claim 7, wherein the flange member comprises a plurality of recesses adapted to allow a user to grasp the tray.

12. The tray of claim 7, wherein the apertures are non-circular.

13. A tray for handling a plurality of syringes, the tray comprising:
   an array of wells adapted for receiving a plurality of syringes;
   the array of wells at least partially defined by a first plurality of ribs and a second plurality of ribs;
   the tray comprising a rectangular shape having a length and a width, the length and the width being substantially perpendicular;
   the first plurality of ribs comprising a plurality of ribs extending in a length direction and being parallel to one another;
   the second plurality of ribs extending in a width direction and being parallel to one another and perpendicular to the first plurality of ribs;
   the first plurality of ribs comprising a greater thickness than the second plurality of ribs, and wherein wells are provided between intersecting ribs, each of the wells comprising a recessed rectangular shape with an aperture provided therein and a support surface configured to support a weight of a syringe in at least one position;
   a flange extending around a perimeter of the tray, the flange comprising an upper surface and a lower surface and wherein the lower surface is adapted to contact a tub;
   each of said apertures being spaced apart along said length and said width; and
   wherein the support surface extends in only one of said width direction and said length direction such that a syringe may only be provided in an aperture in a predetermined orientation.

14. The tray of claim 13, wherein the wells comprise a sidewall, and wherein the sidewall extends downwardly beyond the lower surface of the flange.

15. The tray of claim 14, wherein the sidewalls comprise a first diameter and a second diameter, and wherein the second diameter is greater than the first diameter.

16. The tray of claim 13, wherein the tray comprises a molded plastic material.

17. The tray of claim 13, wherein the flange member comprises a plurality of recesses adapted to allow a user to grasp the tray.

18. The tray of claim 13, wherein the apertures are non-circular.

19. The tray of claim 13, wherein a lower portion of the wells comprise a greater internal diameter than an upper portion of the wells.

20. The tray of claim 13, wherein the tray comprises thirty six wells.

* * * * *